United States Patent
Mark et al.

(10) Patent No.: US 8,062,230 B1
(45) Date of Patent: Nov. 22, 2011

(54) SURGICAL SITE MARKER DELIVERY SYSTEM

(75) Inventors: Joseph L. Mark, Indianapolis, IN (US); Brian Zimmer, Indianapolis, IN (US); Zachary R. Nicoson, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 0 days.

(21) Appl. No.: 11/238,295

(22) Filed: Sep. 28, 2005

Related U.S. Application Data (60) Provisional application No. 60/618,868, filed on Oct. 14, 2004.

(51) Int. Cl.
  *A61B 10/00* (2006.01)
  *A61B 5/05* (2006.01)
  *A61M 36/00* (2006.01)

(52) U.S. Cl. ............. 600/567; 600/7; 600/426; 600/564

(58) Field of Classification Search .................. 600/562, 600/563–572, 7–8, 420, 426–427, 431
See application file for complete search history.

(56) References Cited

U.S. PATENT DOCUMENTS

| | | | |
|---|---|---|---|
| 4,142,517 A * | 3/1979 | Contreras Guerrero de Stavropoulos et al. | 600/567 |
| 4,163,446 A | 8/1979 | Jamshidi | |
| 5,454,378 A | 10/1995 | Palmer et al. | |
| 5,687,739 A * | 11/1997 | McPherson et al. | 600/567 |
| 5,879,357 A | 3/1999 | Heaton et al. | |
| 6,071,301 A | 6/2000 | Cragg et al. | |
| 6,283,941 B1 * | 9/2001 | Schoenfeld et al. | 604/110 |
| 6,371,904 B1 | 4/2002 | Sirimanne et al. | |
| 6,450,938 B1 * | 9/2002 | Miller | 600/7 |
| 6,471,700 B1 * | 10/2002 | Burbank et al. | 606/45 |
| 6,605,047 B2 | 8/2003 | Zarins et al. | |
| 6,662,041 B2 * | 12/2003 | Burbank et al. | 600/431 |
| 6,824,507 B2 | 11/2004 | Miller | |
| 7,104,945 B2 | 9/2006 | Miller | |
| 7,278,972 B2 * | 10/2007 | Lamoureux et al. | 600/567 |
| 2003/0036673 A1 * | 2/2003 | Schmidt | 600/8 |
| 2004/0097981 A1 | 5/2004 | Selis | |
| 2005/0119562 A1 | 6/2005 | Jones et al. | |
| 2005/0228311 A1 * | 10/2005 | Beckman et al. | 600/567 |
| 2005/0277871 A1 | 12/2005 | Selis | |

FOREIGN PATENT DOCUMENTS

WO   WO-2004/012600   2/2004

OTHER PUBLICATIONS

Non-Final Office Action for U.S. Appl. No. 11/518,972 dated Dec. 23, 2008.

(Continued)

*Primary Examiner* — Max Hindenburg
*Assistant Examiner* — H. Q. Nguyen
(74) *Attorney, Agent, or Firm* — Rader, Fishman & Grauer, PLLC (57) ABSTRACT

A site marker delivery system is provided that may be used in combination with a tissue cutting device for marking a biopsy site. The system includes a tube attached to a hub. A push-rod is slidably disposed within the lumen of the tube. The push-rod is advanced forward through the lumen of the tube causing a marker seated within the tube to be deployed at a biopsy site.

11 Claims, 8 Drawing Sheets

OTHER PUBLICATIONS

Response to Non-Final Office Action for U.S. Appl. No. 11/518,972 dated Mar. 18, 2009.
Non-Final Office Action for U.S. Appl. No. 11/518,972 dated Jun. 26, 2009.
Response to Office Action dated Jun. 26, 2009 for U.S. Appl. No. 11/518,972.
Response to Final Office Action dated Dec. 9, 2009 for U.S. Appl. No. 11/518,972.
Final Office Action dated Dec. 9, 2009 for U.S. Appl. No. 11/518,972.
Non-Final Office Action dated Dec. 22, 2010 for U.S. Appl. No. 11/518,972.
Response to Non-Final Office Action dated Dec. 22, 2010 for U.S. Appl. No. 11/518,972.

* cited by examiner

SURGICAL SITE MARKER DELIVERY SYSTEM

CROSS REFERENCE TO RELATED APPLICATIONS

This application claims the benefit of U.S. Provisional Application Ser. No. 60/618,868 filed Oct. 14, 2004 which is hereby incorporated by reference in its entirety.

FIELD OF THE INVENTION

The invention generally relates to a biopsy site marker delivery system that may be used with a biopsy tissue cutting device. More particularly, the invention relates to a biopsy site marker delivery system for non-surgically implanting a site marker at a biopsy.

BACKGROUND OF THE INVENTION

In the field of breast cancer, stereotactically guided and percutaneous biopsy procedures have increased in frequency as well as in accuracy as modern imaging techniques allow the physician to locate lesions with ever increasing precision. However, for a given biopsy procedure, a subsequent examination of the biopsy site is very often desirable.

For example, in those cases where the lesion is found to be benign, a follow-up examination of the biopsy site may be conducted at a later time. Where the lesion is found to be malignant, the physician may want to place additional site markers to help guide the surgeon to the malignancy.

A number of procedures and devices for marking and locating particular tissue locations are known in the prior art. For example, location wire guides are well known for locating lesions, particularly in the breast. One such known device includes a tubular introducer needle and an attached wire guide, which has at its distal end, a helical coil configuration for locking into position about the targeted lesion. The needle is introduced into the breast and guided to the lesion site using an imaging system of a known type, for example, X-Ray, ultrasound or magnetic resonance imaging (MRI), at which time the helical coil at the distant end is deployed about the lesion. Then, the needle may be removed from the wire guide, which remains locked in position distally about the lesion for guiding a surgeon down the wire to the lesion site during subsequent surgery. While such a location system is effective, it is obviously intended and designed to be only temporary, and is removed once the surgery or other procedure has been completed.

It is also known to employ biocompatible dyes or stains to mark breast lesions. First, a syringe containing the colorant is guided to the detection lesion, using an imaging system. Later, during the extraction procedure, the surgeon harvests a tissue sample from the stained tissue. However, while such staining techniques can be effective, it is difficult to precisely localize the stain. Also, the stains are difficult to detect fluoroscopically and may not always be permanent.

Additionally, it is known to implant markers directly into a patient's body using an invasive surgical technique. This enables a practitioner to later return to the site of the graft by identifying the rings, for evaluation purposes.

Each of the above systems and methods for marking a biopsy site has disadvantages associated with effectiveness, accuracy, and invasive surgical techniques. Accordingly, what is needed is a site marker delivery system for delivering a marker to a biopsy site, and deploying the marker at the site effectively, accurately, and without the need for additional invasive surgical procedures.

SUMMARY OF THE INVENTION

In one embodiment of the present invention, the marker delivery system further includes a hub having a proximal end, a distal end and a channel extending between these ends. A tube having a lumen, a proximal end and a distal end, is attachable to the hub proximate the distal end thereof. The tube includes an aperture in communication with the lumen. The aperture is formed through a portion of a side wall of the tube proximate the distal end thereof.

A push-rod is dimensioned to be slidably passed through the channel of the hub and the lumen of the tube to the distal end thereof. The push-rod is operative to advance a marker seated in the lumen of the tube and out of the lumen through the aperture formed in the side wall of the tube.

A tube guide may be provided that is selectively attachable to a non-working end of a tissue cutting device to facilitate the proper alignment of the tube with a channel of the tissue cutting device. The tube guide includes proximal and distal ends and is formed with a channel extending between these ends.

DETAILED DESCRIPTION OF THE INVENTION

An embodiment of a site marker delivery system 10 that may be used in combination with a tissue cutting device for efficiently, accurately and sanitarily depositing a marker at a biopsy site, is disclosed. The marker delivery system 10 includes advantages over conventional delivery devices which are sometimes difficult to use, often result in inaccurate placement of the marker within the biopsy cavity, and allow for relatively large volumes of biological fluids to spill out from the biopsy device onto other equipment, medical professionals, the surrounding work area and floor.

The site marker delivery system 10 is formed of medical grade materials, for example, stainless steel, plastic and rubber. The site marker delivery system 10 includes universal features that allows the system to be used with a number of tissue cutting devices of different sizes, particularly with regard to an inner diameter of an inner cannula and the length of the cutting element of a particular tissue cutting device. The system 10 is adaptable for use in conventional biopsy procedures which may be performed manually and stereotactically. Other advantages provided by the site marker delivery system 10 over conventional marker delivery devices will become apparent from reading the following.

a. Hub

Figures 1, 1A, 1B:
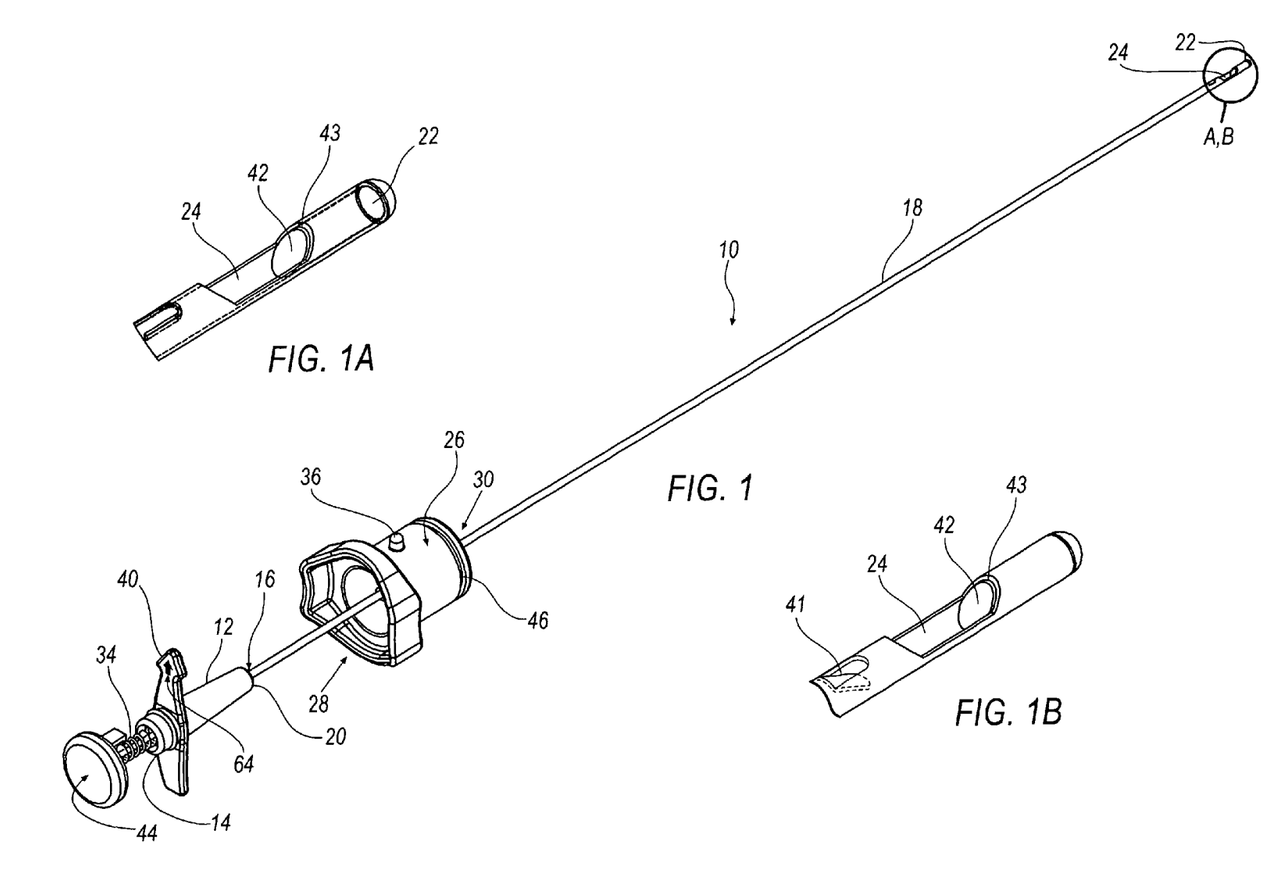
FIG. 1 is a perspective view of an embodiment of a site marker delivery system according to the invention.
FIG. 1A is an enlarged view of a distal end of the site marker delivery system of FIG. 1 in area A after deployment of a site marker.
FIG. 1B is an enlarged view of a distal end of the site marker delivery sytem of FIG. 1 in area A before deployment of a site marker.
Figure 3A:
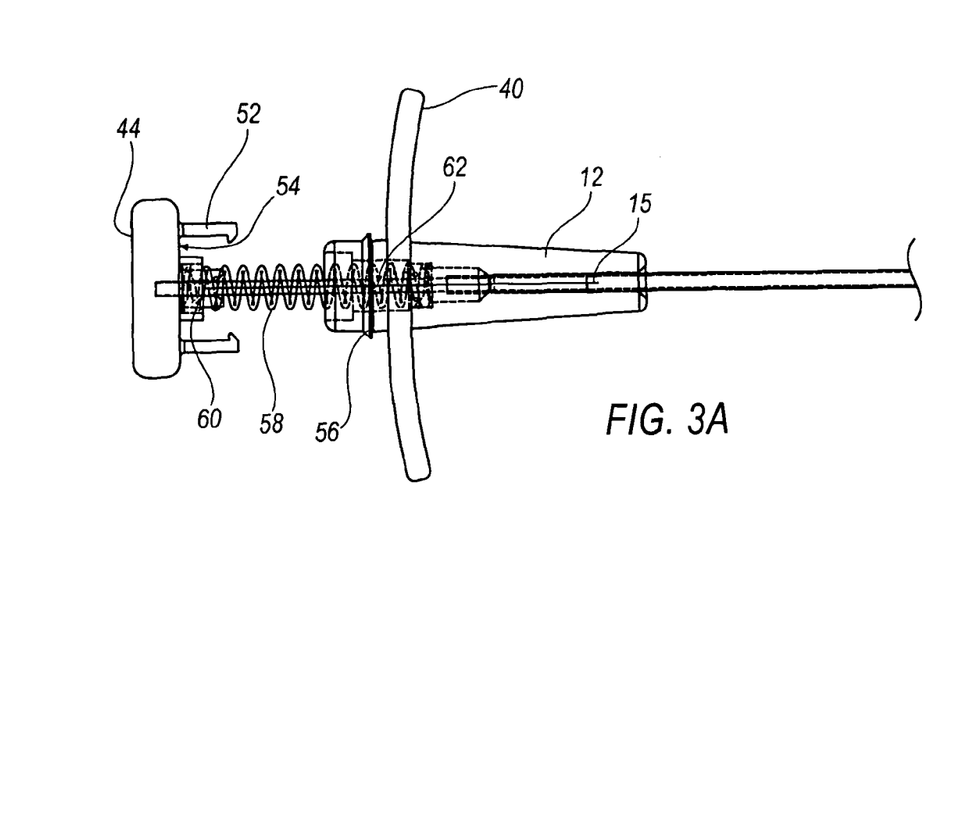
FIG. 3A is an enlarged view of the hub and deployment trigger of the embodiment of the site marker delivery system of FIG. 1 in a first position.
Figure 3B:
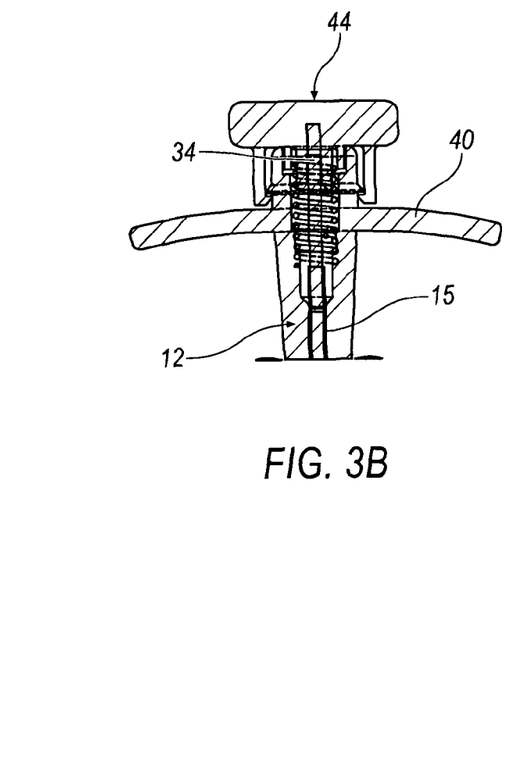
FIG. 3B is an enlarged view of the hub and deployment trigger of the embodiment of the site marker delivery system of FIG. 1 in a second position.

FIG. 1 illustrates an embodiment of a site marker delivery system 10 according to the invention. The marker delivery system 10 includes a hub 12 having a proximal end 14 and a distal end 16. The hub 12 is formed with a channel 15 (as best seen in FIGS. 3A-3B) that extends between the proximal 14 and distal 16 ends.

In one embodiment, the hub 12 includes a tactile indicator 40 adjacent the proximal end 14 that is indicative of the circumferential orientation of an aperture 24 of a tube 18 to be described hereinafter. The tactile indicator 40 may include a marking 64 that allows the indicator 40 to be visible in low light conditions as an additional means of indicating the orientation of the aperture 24 of the tube 18.

b. Tube

Figure 4A:
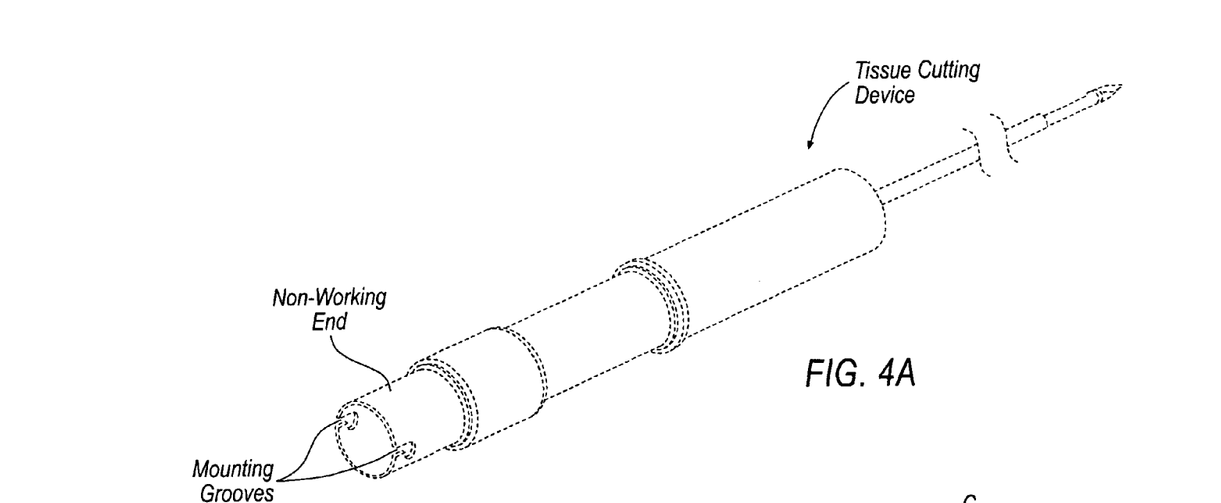
FIG. 4A is a perspective view of a tissue cutting device that may be used with the embodiment of the site marker delivery system of FIG. 1.
Figure 4B:
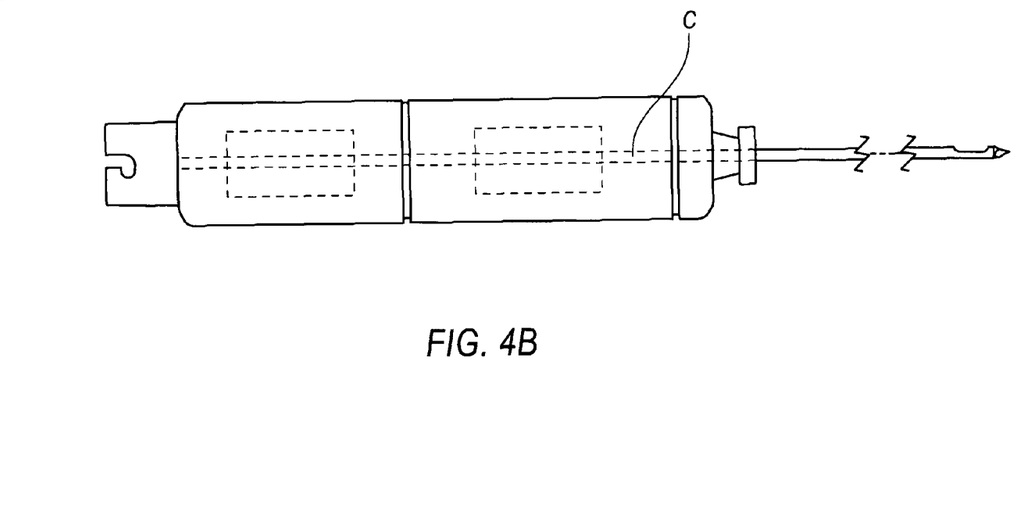
FIG. 4B is a cross-section of the tissue cutting device of FIG. 4A illustrating the channel formed along the longitudinal access of the tissue cutting device.

A tube 18 having a lumen (not shown) is provided having a proximal end 20 and distal end 22. The tube 18 is fixedly attachable to the hub 12 adjacent the distal end 16 of the hub 12. As mentioned above, the tube 18 includes an aperture 24 that is in communication with the lumen. The aperture 24 is formed through a portion of a side-wall of the tube 18 proximate the distal end 22. In one embodiment, the tube 18 is dimensioned to slidably pass through a channel C of a tissue cutting device (See FIG. 4B).

The tube 18 is preferably formed of a substantially rigid medical grade material such as stainless steel, plastic or other materials suitable. A marker (M) may be seated within the tube 18. It is preferred that the marker M is seated adjacent a proximal end of the aperture 24 (See FIG. 6). To retain marker M within tube 18 at least one retention tab 41 may be provided. Prior to deployment, retention tab 41 is depressed inwardly from an outer surface of tube 18 so as to form a lip to prevent a marker M from prematurely deploying out of aperture 24 (See FIG. 1B). Once ejection of the marker M is facilitated (to be explained in further detail below), the marker M is pushed against retention tab 41, overcoming the spring force in retention tab 41 such that retention tab 41 is forced upwardly (See FIG. 1A) to allow passage of marker M through to aperture 24.

In one embodiment, the tube may further include an inclined wall 42 formed proximate a distal end 43 of the aperture 24 (See FIG. 1A). The inclined wall 42 operates as a ramp that assists in facilitating the ejection of the marker M out of the aperture 24 (to be explained in further detail below).

c. Tube Guide

A tube guide 26 may be provided. The tube guide 26 is selectively attachable to a non-working end of a tissue cutting device, wherein a portion of the tube guide 26 is received in a cavity 27 formed in the non-working end of the tissue cutting device. The tube guide 26 includes a proximal end 28 and a distal end 30. The tube guide 26 is formed with a channel 32 that extends between the proximal 28 and distal 30 ends (See FIG. 5).

Preferably, the tube guide 26 includes at least one attachment pin 36 disposed on an exterior wall thereof. The attachment pin 36 is constructed for engaging a complimentary mounting groove 38 formed on the non-working end of the tissue cutting device so as to key the tube guide to the tissue cutting device. After the tube guide 26 is keyed to the tissue cutting device, the channel 32 of the tube guide 26 is longitudinally aligned with the channel C of the tissue cutting device. Accordingly, tube guide 26 operates to maintain the orientation between the marker delivery system 10 and the tissue cutting device.

Figure 6:
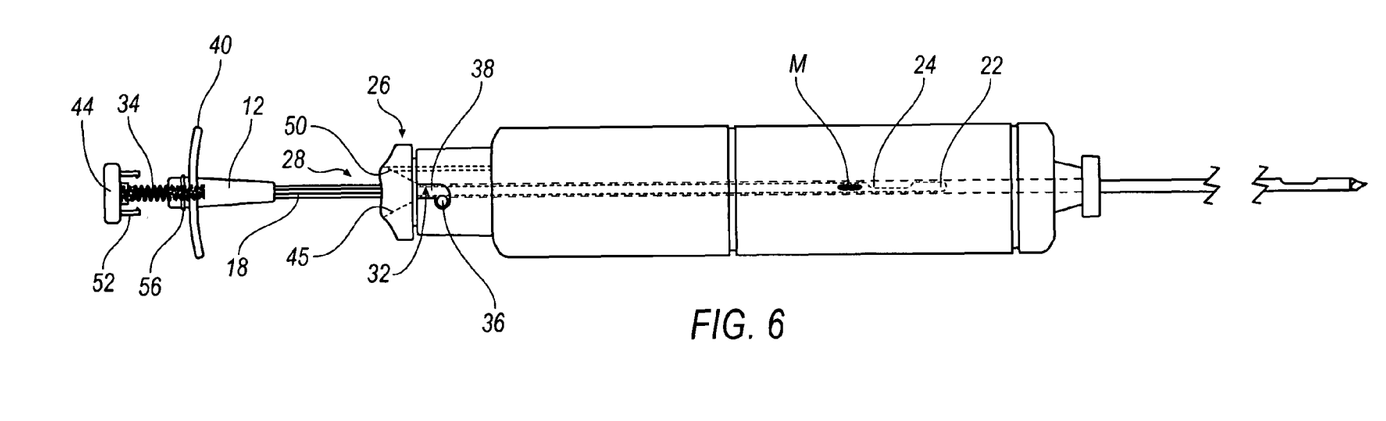
FIG. 6 is a side view of the site marker delivery system of FIG. 1A in a first position prior to deployment of the site marker.
Figure 7:
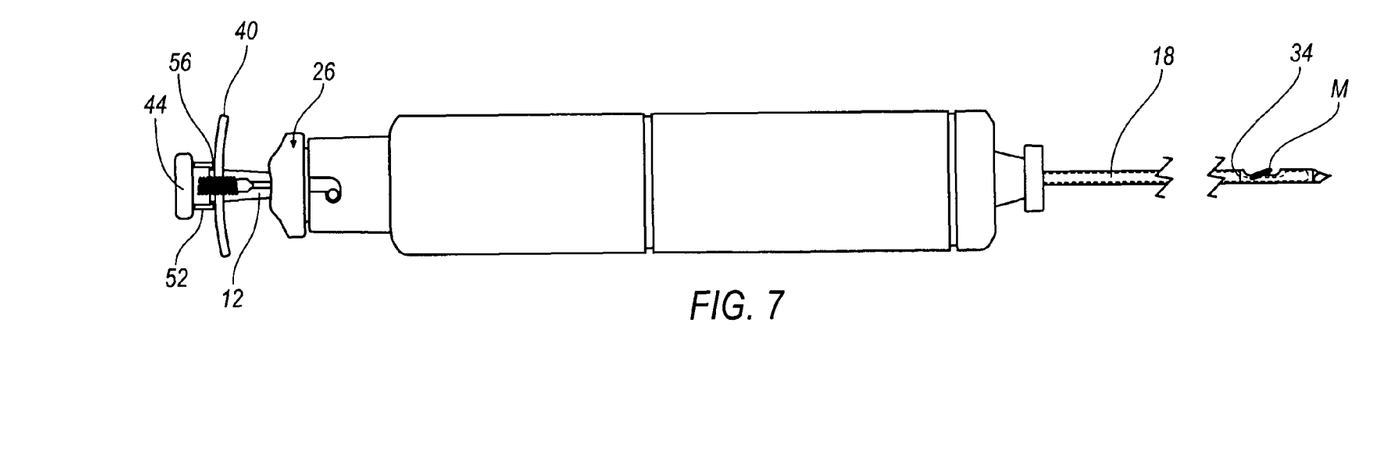
FIG. 7 is a side view of the site marker delivery system of FIG. 1 attached to the tissue cutting device in a second position after the site marker has been deployed.

As best illustrated in FIG. 6, the proximal end 28 of the tube guide 26 is formed as a funnel shaped wall 45. The funnel shaped wall 45 operates to direct the tube 18 into the channel 32 of the tube guide 26 such that the tube 18 can be advanced through the channel C of the tissue cutting device. In this fashion, the tube 18 can be directed into the channel 32 of the tube guide without having to visibly guide the tube 18 into the channel 32, unlike conventional marker delivery devices that required that the apparatus holding the markers be visibly guided into a channel C of a tissue cutting device.

Figures 5, 5A:
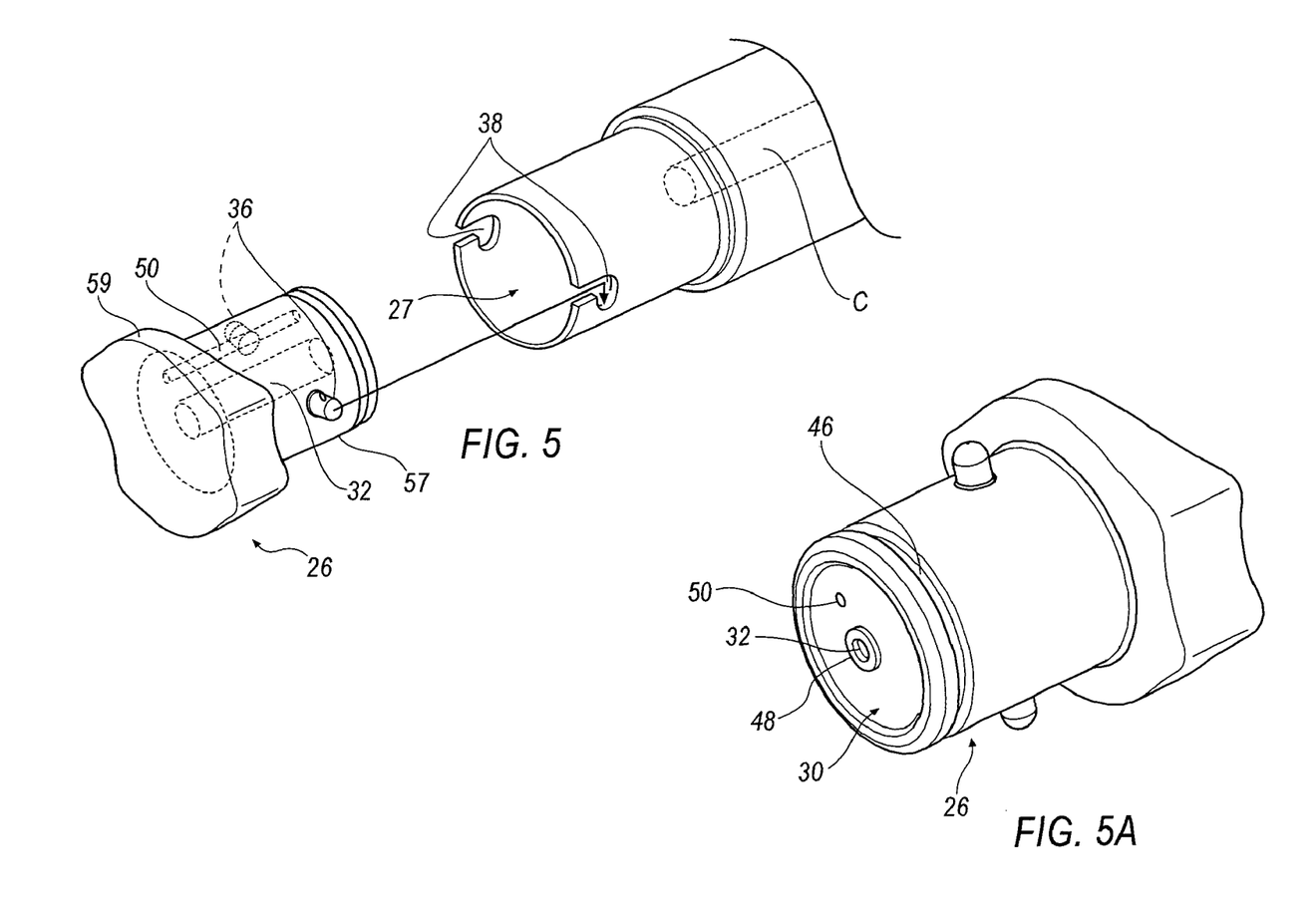
FIG. 5 is a fragmentary view of the tissue cutting device of FIG. 4A and the tube guide of the embodiment of FIG. 1.
FIG. 5A is an enlarged view of the tube guide of the site marker delivery system of FIG. 1.

As shown in FIG. 5A, the tube guide 26 preferably includes a first fluid sealing ring 46 disposed on its exterior wall adjacent the distal end 30 and a second fluid sealing ring 48 disposed within the channel 32 adjacent the distal end 30. The first and second fluid sealing rings 46, 48 operate to prevent bodily fluids from spilling out through the tissue cutting device or the site marker delivery system when the biopsy site is being marked. This helps maintain a safe, clean, and sanitary environment for medical personnel and patients.

The tube guide 26 may also include an air venting aperture 50 that has an inner diameter less than an inner diameter of the channel 32 of the tube guide 26. The disparate diameters insures that the tube 18 cannot be erroneously fitted into the air venting aperture 50 causing it to be out of alignment with the channel C of the tissue cutting device.

d. Push-Rod

A push-rod 34 is dimensioned to slidably pass through the channel 15 of the hub 12 and the lumen of the tube 18 to the distal end 22 of the tube 18. The push-rod 34 is operable to advance the marker M seated in the lumen of the tube 18 out of the lumen through the aperture 24. In one embodiment, the push-rod 34 has an outer diameter that is substantially contiguous with the lumen of the tube 18. In this fashion, the push-rod 34 operates to close or block the aperture 24 such that after the marker M has been deployed it can not fall back into the aperture 24.

e. Deployment Trigger

Figure 2:
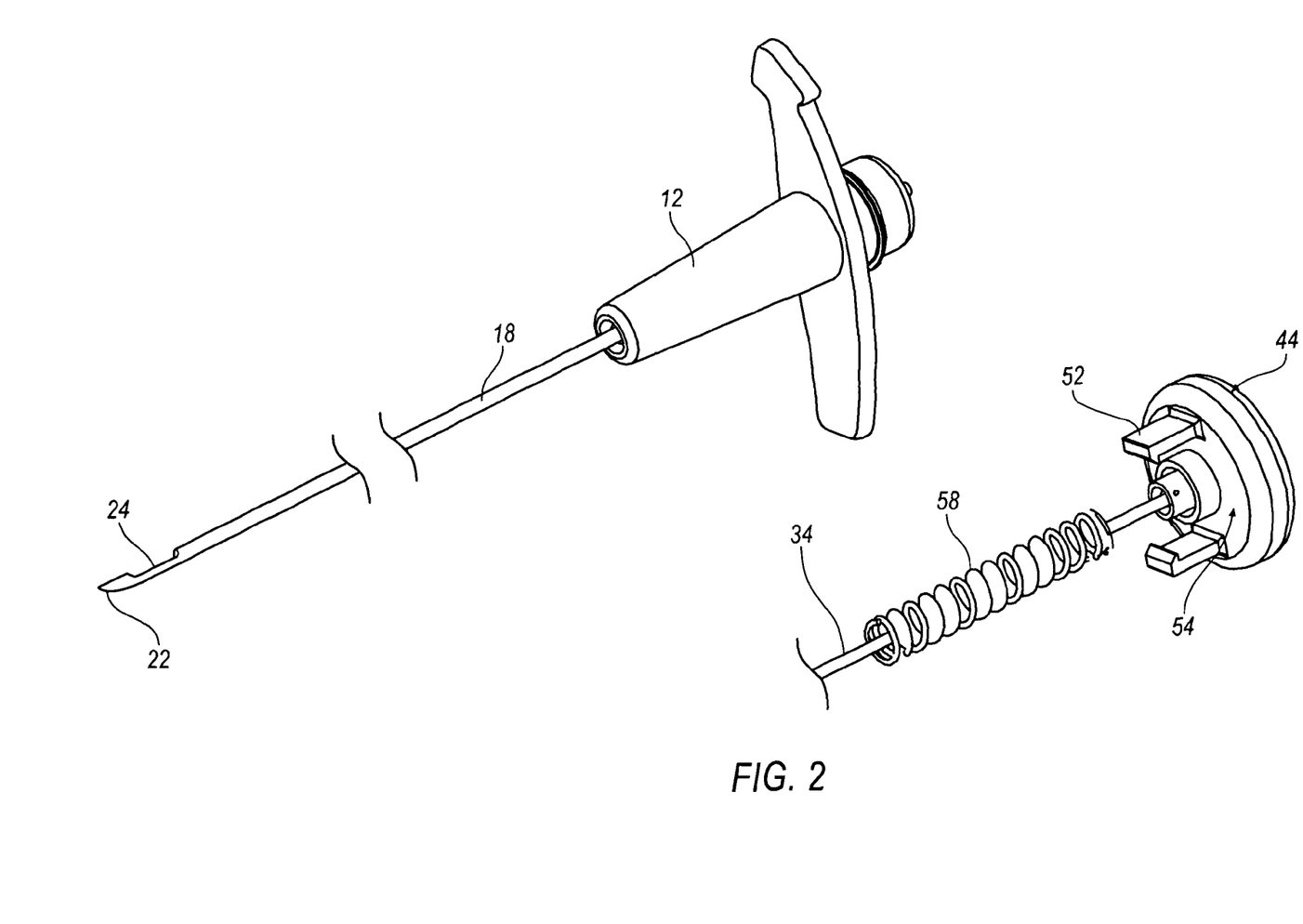
FIG. 2 is an exploded view of the embodiment of the site marker delivery system of FIG. 1.

The site marker delivery system 10 preferably also includes a deployment trigger 44 that is selectively attachable to the proximal end 14 of the hub 12. As seen in FIG. 2, the push rod 34 is attachable to a first surface 54 of the deployment trigger 44 such that the deployment trigger 44 is operable to advance the push rod 24 toward the distal end 22 of the tube 18 when the deployment trigger 44 is being attached to the proximal end 14 of the hub 12.

Preferably, the deployment trigger 44 is formed as a push plate having opposing surfaces and at least one retaining arm 52 extending from the first surface 54. The at least one retaining arm 52 operates to engage a complimentary retaining rim 56 (best seen in FIG. 3A) disposed adjacent the proximal end 14 of the hub 12. The engagement of the at least one retaining arm 52 and the retaining rim 56 operates to lock the push rod 34 in place after the marker has been advanced out through the aperture 24 of the tube 18. The engagement procedure provides a tactile and audible indication to the user of the site marker delivery system 10 that the marker has been deployed. The tactile indication is force feedback from snapping the at least one retaining arm 52 onto the retaining rim 56. The audible indication is provided by the user actually hearing a "snapping" sound when the deployment trigger 44 is engaged with the hub 12.

As best illustrated in FIG. 3A, the deployment trigger 44 also includes a spring 58 disposed between the proximal end 14 of the hub 12 and the deployment trigger 44. The spring 58 concentrically surrounds a proximal end of the push rod 34 wherein a first end 60 of the spring 58 frictionally engages a central portion of the deployment trigger 44 and a second end 62 of the spring 58 frictionally engages the proximal end 14 of the hub 12. The spring 58 is adapted to maintain the longitudinal alignment between the deployment trigger 44 and the proximal end 14 of the hub 12. This allows for the push-rod 34 to be substantially stabilized when being axially advanced toward the distal end 22 of the tube 18.

f. Method of Using the Marker Delivery System

Figure 8:
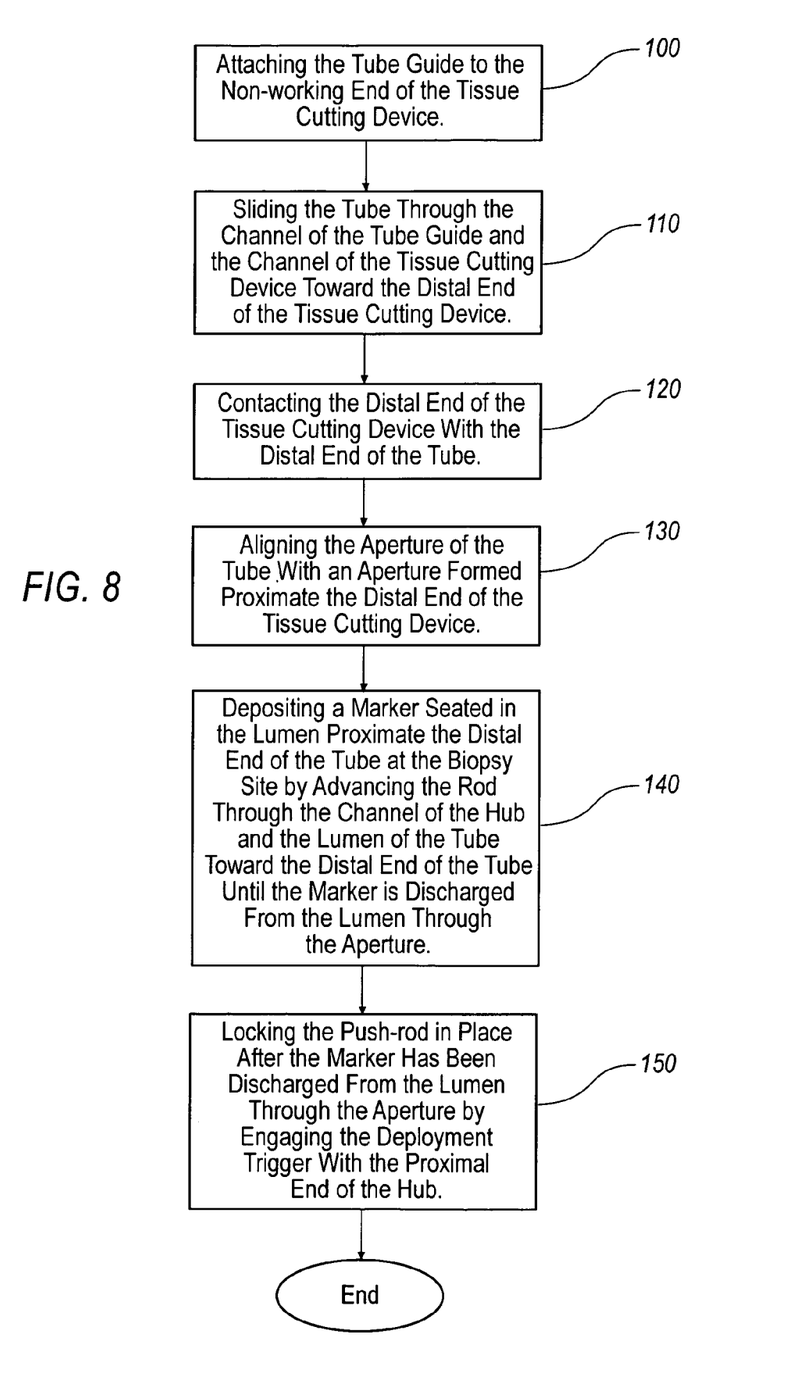
FIG. 8 is a flow diagram of a method of using the site marker delivery system of FIG. 1 to mark a biopsy site.

FIG. 8 illustrates a method of using the site marker delivery system 10 in combination with a tissue cutting device for the purpose of marking a biopsy site. The method begins at 100 with attaching the tube guide 26 to the non-working end of the tissue cutting device. This step ensures that the channel 32 of the tube guide 26 is in alignment with the channel C of the tissue cutting device.

At 110, the method continues by sliding the tube 18 through the channel 32 of the tube guide 26 and the channel C of the tissue cutting device toward the distal end of the tissue cutting device.

At 120, the user of the site marker delivery system 10 receives a tactile indication from contacting the distal end of the tissue cutting device with the distal end 22 of the tube 18. This indicates that the marker delivery system 10 is in position for deployment of the site marker.

At 130, the method continues by aligning the aperture 24 of the tube 18 with an aperture formed proximate the distal end of the tissue cutting device. The tactile indicator 40 assists the user in orientating the aperture 24 with the aperture in the tissue cutting device. The method advances to 140.

At 140, the biopsy site is marked by depositing a marker seated in the lumen of the tube 18 at the biopsy site. This is accomplished by advancing the push-rod 34 through the channel 15 of the hub 12 and the lumen of the tube 18 toward the distal end 22 of the tube 18 until the marker M is discharged from the lumen and out through the aperture 24. If a retention tab 41 is provided, this step may also pushing retention tab 41 upwardly such that marker M may be advanced to the aperture 24 by push-rod 34.

At 150, the push-rod is locked in place after the marker M has been discharged from the lumen through the aperture 24 by engaging the deployment trigger 44 onto the proximal end 14 of the hub 12. In this fashion, the push rod 34 operates to prevent the marker from falling back into the aperture 24 during removal of the side marker delivery system 10 and the tissue cutting device from the biopsy site.

Figure 9:
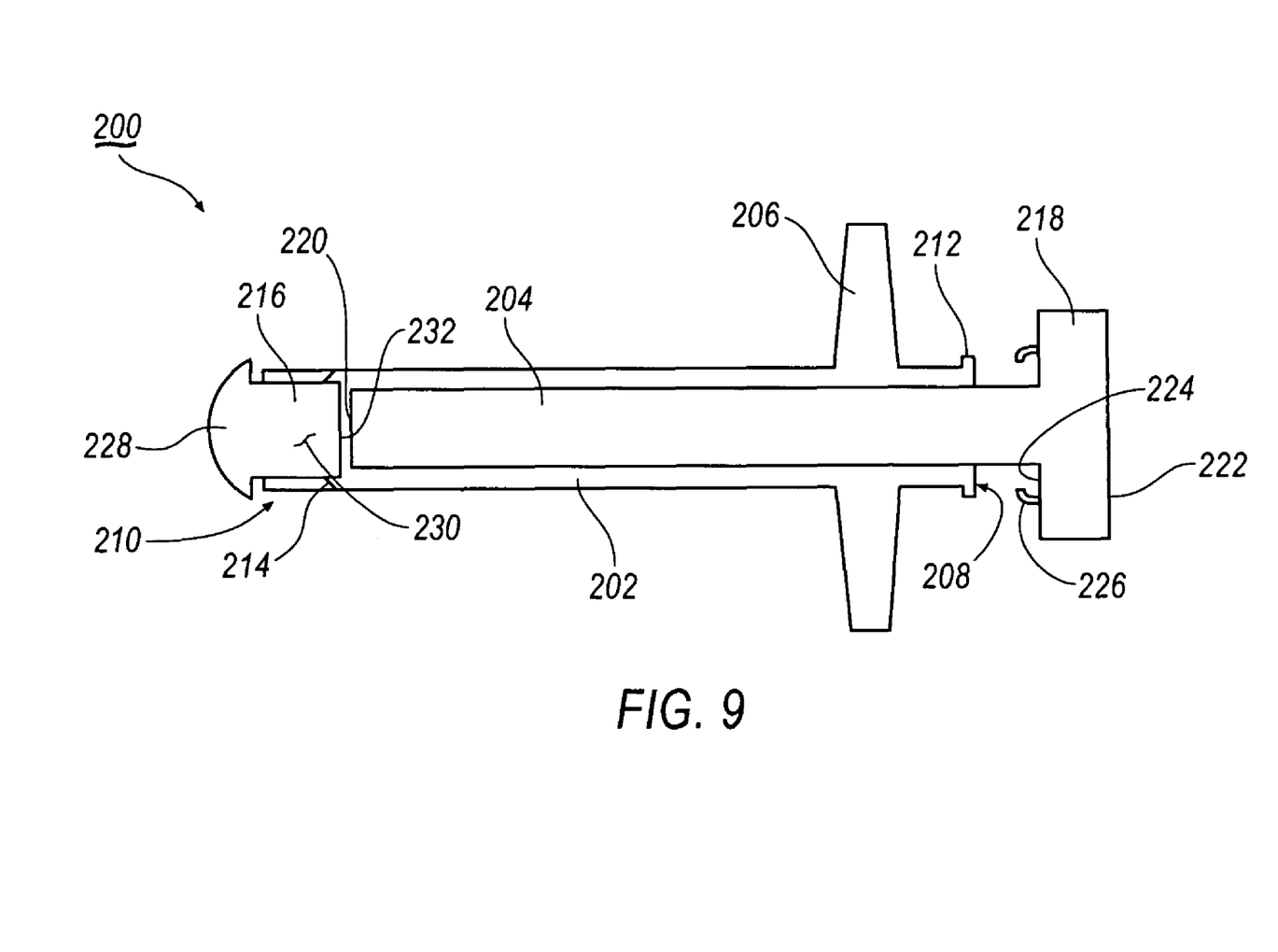
FIG. 9 is an alternative embodiment of a site marker delivery system.

Referring now to FIG. 9, an alternative embodiment of an end deployment site marker delivery system 200 is shown. End deployment site marker delivery system 200 includes a cannula 202, a push rod 204, and a handle 206. Cannula 202 is hollow and defines an inner lumen having a proximal end 208 and a distal end 210. Both proximal and distal ends 208 and 210 are open. In one embodiment, proximal end 208 further includes at least one retaining rim 212 (to be explained in further detail below).

In one embodiment, positioned slightly inboard of distal end 210 is at least one holding tab 214. Holding tab 214 is formed on an internal surface of cannula 202 and is sized so as to frictionally engage a portion of a site marker 216 (to be explained in further detail below). In one embodiment holding tab 214 is constructed of a suitable material having a predetermined degree of flexibility such that a predetermined amount of force may flex the holding tab out of engagement with site marker 216.

Push rod 204 is connected to a deployment plunger 218 at its proximal end. Push rod 204 further includes a distal end 220 that is selectively contactable with site marker 216. Push rod 204 is dimensioned to slidably pass through the lumen of cannula 202 to the distal end 210 of cannula 202. However, push rod 204 further may be dimensioned so as to be substantially contiguous with the lumen of cannula 202 to block or close open distal end 210 such that after marker 216 has been deployed, it cannot reenter cannula 202.

Deployment plunger 218 is formed as a push plate having opposing surfaces 222, 224 and at least one retaining arm 226 extending from one of the opposing surfaces 222. Retaining arm 226 operates to engage retaining rim 212 of cannula 202 in a complementary fashion. Engagement of retaining arm 226 and retaining rim 212 operates to lock push rod 204 in place after marker 216 has been advanced out though distal end 210. The engagement of retaining arm 226 and 212 provides a tactile (force feedback from snapping retaining arm 226 onto retaining rim 212) and audible (the "snapping" sound generated when retaining arm 226 engages retaining rim 212) indication to the user of site marker delivery system 200 that marker 216 has been deployed.

Handle 206 is connected to cannula 202. In one embodiment, handle 206 is integrally formed with cannula 202. Handle 206 provides a convenient gripping portion for grasping cannula 202 to maintain the position of cannula 202 while activating the deployment plunger 218.

Marker 216 is positioned within open distal end 210 of cannula. In one embodiment, marker 216 includes a head portion 228 and a body portion 230, where head portion 228 is sized to be at least slightly larger than the outside diameter of cannula 202 such that head portion 228 remains outside of the lumen of cannula 202. While head portion 228 is configured as a "cap" in FIG. 9, it is understood that other geometries may be employed for head portion 228 such as a blunt end or a trocar tip. Further, it is also understood that marker 216 need not be provided with a head portion 228 at all.

Body portion 230 is sized to at least partially slidably pass into distal end 210 of cannula 202. However, body portion 230 is also sized such that it frictionally engages holding tab 214. Holding tab 214 retains marker 216 to cannula 202 until it is deployed via push rod 204.

When deployment plunger 218 is activated, push rod 204 moves through cannula 202 until distal end 220 of push rod 204 comes into contact with an end 232 of body portion 230. Push rod 204 then over comes the frictional force of holding tab 214 and pushes marker 216 out through distal end 210 of cannula 202 into the body cavity. When deployment plunger 218 has reached distal end 210 of cannula 202, retaining arm 226 engages retaining rim 212 thereby indicating deployment of marker 216.

The foregoing embodiments of the site marker delivery system is disclosed for illustrative purposes. Many adaptations and modifications will become apparent to one of ordinary skill in the art upon reading the above descriptions. The scope of the invention should be determined with reference to the appended claims, along with the full scope of equivalence to which such claims are entitled.

We claim:

1. A method of marking a biopsy site using a marker delivery system in combination with a tissue cutting device, comprising the steps of:
   positively attaching a tube guide to a non-working end of a tissue cutting device such that the tube guide is selectively and fixedly secured to the tissue device, wherein a portion of the tube guide is received in a cavity formed in the non-working end of the tissue cutting device, but the tube guide does not extend into a channel that is in communication with the cavity, the channel extending through the tissue cutting device;
   wherein the tube guide is provided with a channel therein, and once the tube guide and the tissue cutting device are positively attached together, an end face of the channel of the tube guide directly contacts and aligns with an end face of the channel in the tissue device, such that the end face of the channel of the tube guide and the end face of the channel of the tissue cutting device abut to form a single integrated channel having a constant diameter, wherein the single integrated channel defines a continuous and uninterrupted pathway through the tube guide and the tissue cutting device, and where the cavity formed in the non-working end of the tissue cutting device is configured for aligning the channel of the tube guide with the channel of the tissue cutting device;
   wherein the single integrated channel that defines the continuous and uninterrupted pathway from the tube guide to the channel of the tissue cutting device by way of the channel of the tube guide, maintains the orientation between the marker delivery system and the tissue cutting device;
   sliding a tube through the single integrated channel that defines the continuous and uninterrupted pathway formed by the channel of the tube guide and the channel of the tissue cutting device toward a distal end of the tissue cutting device;
   aligning an aperture of the tube with an aperture formed proximate the distal end in a sidewall of the tissue cutting device while the tissue cutting device is positioned in a body; and
   depositing a marker seated in a lumen of the tube at the biopsy site by advancing a push rod through the channel of the tube guide and the lumen of the tube toward a distal end of the tube until the marker is discharged from the lumen through the aperture of the tube formed therein and through the aperture of the tissue cutting device.

2. The method of claim 1 further comprising the step of contacting the distal end of the tissue cutting device with the distal end of the tube.

3. The method of claim 1 further comprising the step of utilizing a visual indicator to align the aperture of the tube with the aperture of the tissue cutting device.

4. The method of claim 1 further comprising the step of locking the push rod in place such that the push rod cannot move after the marker has been discharged from the lumen through the aperture of the tube formed therein.

5. The method of claim 1, wherein said step of attaching the tube guide to the non-working end of the tissue cutting device further includes locking the tube guide to the non-working end of the tissue cutting device in a predetermined orientation such that the tube guide is fixedly secured to the tissue cutting device.

6. The method of claim 1, further comprising providing at least one seal mechanism that cooperates with the tissue cutting device and the tube guide such that the step of attaching the tube guide to the non-working end of the tissue cutting device further includes sealingly engaging the tube guide and the tissue cutting device through the direct contact.

7. The method of claim 6, further comprising:
   providing a first seal mechanism that cooperates with the channel of the tissue cutting device and the channel of the tube guide; and
   providing a second seal mechanism that cooperates with non-working end of the tissue cutting device and the portion of the tube guide that is received within the non-working end of the tissue cutting device;
   wherein the step of attaching the tube guide to the non-working end of the tissue cutting device engages the first and second seal mechanisms between the tissue cutting device and the tube guide to sealingly engage the tube guide and the tissue cutting device.

8. The method of claim 1, wherein the tube guide further comprises a funnel shaped wall that slopes toward the channel of the tube guide such that when the tube is positioned within the tube guide, the funnel shaped wall cooperates to direct the distal end of the tube to the channel of the tube guide.

9. The method of claim 4 further comprising locking at least one retaining arm extending from a push plate to a retaining rim extending outwardly from a hub configured to be fixedly attachable to the tube.

10. The method of claim 1 further comprising the step of compressing a biasing means concentrically surrounding a proximal end of the push rod.

11. The method of claim 10 wherein the biasing means is a spring configured to frictionally engage a central portion of a deployment trigger and a proximal end of a hub fixedly attached to the tube, such that the spring advances the push rod distally.

* * * * *